US006472533B1

(12) United States Patent
Burgess

(10) Patent No.: US 6,472,533 B1
(45) Date of Patent: Oct. 29, 2002

(54) LIGANDS FOR CHIRAL CATALYSIS

(75) Inventor: Kevin Burgess, Bryan, TX (US)

(73) Assignee: The Texas A & M University System, College Station, TX (US)

( * ) Notice: Subject to any disclaimer, the term of this patent is extended or adjusted under 35 U.S.C. 154(b) by 0 days.

(21) Appl. No.: 09/520,347

(22) Filed: Mar. 7, 2000

Related U.S. Application Data

(60) Provisional application No. 60/128,359, filed on Apr. 8, 1999.

(51) Int. Cl.[7] .................................................. C07F 9/28
(52) U.S. Cl. ........................................ 548/119; 548/237
(58) Field of Search ............................. 548/119, 237

(56) References Cited

U.S. PATENT DOCUMENTS

| 4,963,671 A | 10/1990 | Krapcho ..................... 540/491 |
| 5,693,820 A | * 12/1997 | Helmchen et al. .......... 548/101 |

FOREIGN PATENT DOCUMENTS

| DE | 42 43 030 A1 | 6/1994 |
| EP | 0 278 621 | 8/1988 |
| WO | WO 89/12633 | 12/1989 |
| WO | WO 94/10127 | 5/1994 |
| WO | WO 97/48681 | 12/1997 |
| WO | WO 98/50030 | 11/1998 |

OTHER PUBLICATIONS

Chemical Abstracts 129:289719, 1999.
Chemical Abstracts 129:275632, 1998.
Porte et al, J. Am. Chem. Soc., 120:9180–9187 (1998).
Burgess et al, Tetrahedron: Asymmetry, 9:2465–2469 (1998).
Meyers et al, Synthesis, pp. 250–262 (1993).
Ksander et al, J. Med. Chem., 40:495–505 (1997).
Braghiroli et al, Tetrahedron Asymmetry, 8(13):2209–2213 (1997).
Kanai et al, Tetrahedron, 55:3843–3854 (1999).
Zarrinmayeh et al, Journal of Medicinal Chemistry, 41(15):2709–2719 (1998).
Williams et al, J. Am. Chem. Soc., 113:9276–9286 (1991).
Williams et al, J. Am. Chem. Soc., 110:1547–1557 (1988).
Desimoni et al, Tetrahedron, 51(14):4131–4144 (1995).

* cited by examiner

*Primary Examiner*—Floyd D. Higel
*Assistant Examiner*—Kamal Saeed
(74) *Attorney, Agent, or Firm*—Morgan, Lewis & Bockius, LLP

(57) ABSTRACT

Novel phosphine oxazoline ligands of formula (I)

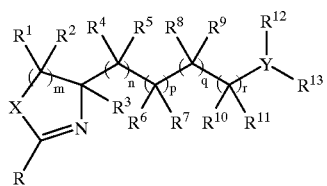

wherein
  m is 1, 2, 3 or 4;
  n, p, q, r are independently zero or 1 provided that at least one of n, p, q and r is 1;
  X is O, S, Se, $CH_2$, NH;
  Y is N, P, As, S;
  R is H; a straight, branched or cyclo alkyl optionally substituted by one or more groups independently selected from alkyl, aryl, halo, alkoxy, amine, phosphine, ether; aryl optionally substituted by one or more groups independently selected from alkyl, aryl, halo, alkoxy, amine, phosphine, ether; ferrocenyl; a thioalkyl group; a thioaryl group; or R is part of a polymeric structure, for example polyacrylic acid;
  $R^1$ to $R^{13}$ are independently selected from H; a straight, branched or cyclo alkyl optionally substituted by one or more groups independently selected from alkyl, aryl, halo, alkoxy, amine, phosphine, ether; aryl optionally substituted by one or more groups independently selected from alkyl, aryl, halo, alkoxy, amine, phosphine, ether;

a process for the preparation thereof, metal complexes containing such ligands and the use of such complexes, or combinations of ligand with metal salts or complexes, as catalysts for asymmetric syntheses is disclosed.

12 Claims, No Drawings

LIGANDS FOR CHIRAL CATALYSIS

This application claims the benefit of U.S. Provisional Application No. 60/128,359, filed Apr 8, 1999.

The present invention relates to novel optically active phosphine oxazoline ligands, a process for the preparation thereof, metal complexes containing such novel ligands and the use of such complexes, or combinations of ligand with metal salts or complexes, as catalysts for asymmetric syntheses.

The development of novel catalytic systems exhibiting unique reactivity and high enantioselectivity is of great importance in science and technology. The activity of many pharmaceuticals, agrochemicals, fragrances and food additives are associated with a specific enantiomer. Thus, the ability to produce enantiomerically pure compounds is essential. Many approaches have been explored to acquire such enantiomerically pure compounds, ranging from optical resolution and structural modification of naturally occurring chiral substances to asymmetric catalysis using synthetic chiral catalysts and enzymes. Asymmetric catalysis has been found to be one of the most efficient, if not the most efficient method of producing enantiomerically pure compounds since a small amount of a chiral catalyst can be used to produce a large quantity of a chiral compound.

One class of ligands which have played a significant role in the development of chiral catalysts are asymmetric phosphine ligands. Although over 1000 chiral diphosphine ligands have been prepared since the application of the DIPAMP ligand in the production of L-Dopa, only a few of these have the efficiency and selectivity of commercial applications. Some of the most well known phosphine ligands used include BINAP, BPPM, DEGPHOS, DIOP, Chiraphos, Skewphos, Duphos and BPE. However, these ligands have their disadvantages and are not ideal for all applications.

There is still, therefore, the need to develop novel chiral catalysts which are highly enantiomerically selective and carry out the required reaction giving a high yield.

Accordingly, the present invention provides a phosphine oxazoline ligand of formula (I)

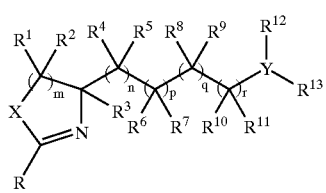

wherein
m is 1, 2, 3 or 4;
n, p, q, r are independently zero or 1 provided that at least one of n, p, q and r is 1;
X is O, S, Se, $CH_2$, NH;
Y is N, P, As, S;
R is H; a straight, branched or cyclo alkyl optionally substituted by one or more groups independently selected from alkyl, aryl, halo, alkoxy, amine, phosphine, ether; aryl optionally substituted by one or more groups independently selected from alkyl, aryl, halo, alkoxy, amine, phosphine, ether; ferrocenyl; a thioalkyl group; a thioaryl group; or R is part of a polymeric structure, for example polyacrylic acid;
$R^1$ to $R^{13}$ are independently selected from H; a straight, branched or cyclo alkyl optionally substituted by one or more groups independently selected from alkyl, aryl, halo, alkoxy, amine, phosphine, ether; aryl optionally substituted by one or more groups independently selected from alkyl, aryl, halo, alkoxy, amine, phosphine, ether.

By the term "alkyl" we mean a straight, branched or cyclo alkyl group having any number of carbon atoms, for example from 1 to 14 carbon atoms, such as from 1 to 10 carbon atoms. The cyclo alkyl groups may have only one or more than one ring structure e.g. adamantyl.

By the term "aryl" we mean an aromatic monovalent hydrocarbon radical, for example phenyl, benzyl, naphthyl, etc.

Suitably, m is 1 or 2; preferably 1.
Suitably, at least two of n, p, q and r are 1, the remaining two being zero or 1; preferably, two of n, p, q and r are 1, the remaining two being zero.
Suitably, X is O, S, $CH_2$ or NH; preferably O.
Suitably, Y is P, N or S; preferably P.

A first embodiment of the invention provides a compound of formula (IA)

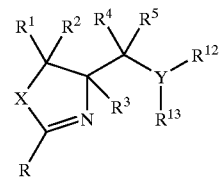

wherein m, X, Y, R, and $R^1$ to $R^5$ and $R^{12}$ and $R^{13}$ are as hereinbefore defined.

A second embodiment of the invention provides a compound of formula (IB)

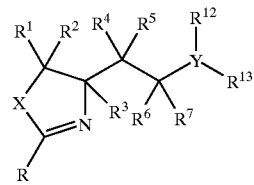

wherein m, X, Y, R and $R^1$ to $R^7$ and $R^{12}$ and $R^{13}$ are as hereinbefore defined.

A third embodiment of the invention provides a compound of formula (IC)

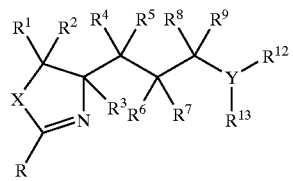

wherein m, X, Y, R and R to $R^1$ and $R^{12}$ and $R^{13}$ are as hereinbefore defined.

A fourth embodiment of the invention provides a compound of formula (ID)

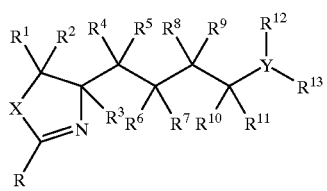

ID wherein m, X, Y, R and $R^1$ to $R^{13}$ are as hereinbefore defined.

A particularly preferred embodiment of the invention provides a compound of the following structure:

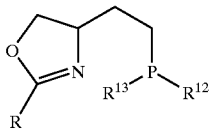

wherein R is $C_{1-4}$ alkyl optionally substituted by one or more groups selected from phenyl or halo; phenyl optionally substituted by one to five substituents selected from the group consisting of halo, $C_{1-4}$ alkyl, $C_{1-4}$ alkoxy or nitro; ferrocenyl or adamantyl; and $R^{12}$ and $R^{13}$ are Ph or cyclohexyl.

Particularly preferred compounds include those of the following formulae:

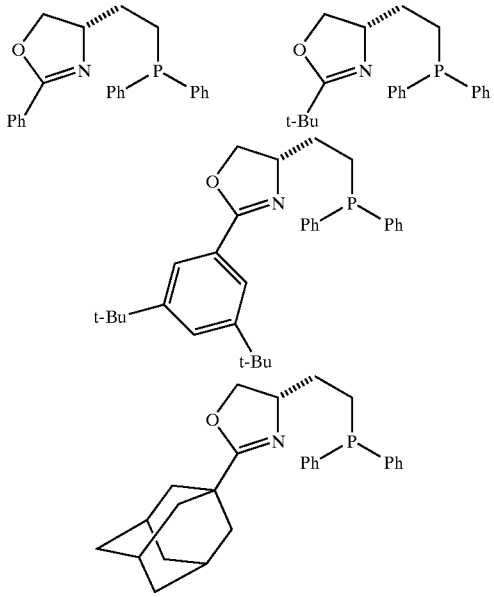

Compounds of formula (I) are novel and. accordingly a further aspect. of the resent invention provides a process for the preparation of a compound of formula (I). compounds of formula (I) may be prepared by the reaction of a compound of formula (II)

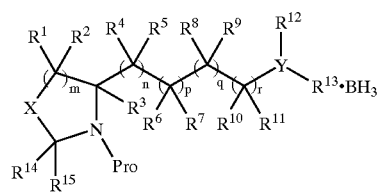

II wherein m, n, p, q, r, X, Y and $R^1$ to $R^{13}$ are as hereinbefore defined; $R^{14}$ and $R^{15}$ are alkyl groups which may be the same of different and Pro is a nitrogen protecting group, for example BOC, with a compound of formula (III)

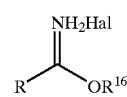

III wherein R is as hereinbefore defined, $R^{16}$ is an alkyl group, for example ethyl, and Hal is a halogen atom, for example chloro. The reaction is carried out by the addition of for example gaseous HCl, in the presence of an alcohol, such as methanol to the compound of formula (II), followed by the addition of a compound of formula (III) in the presence of a base, for example triethylamine, in a suitable solvent such as dichloromethane.

Compounds of formula (III) are known in the literature (Meyers, A. I.; Schmidt, W; McKennon, M. J., Synthesis, 1993, 250–262).

Compounds of formula (II) may be prepared by the reaction of a compound of formula (IV)

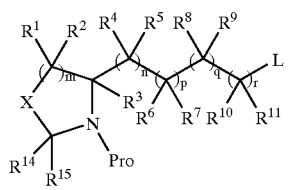

IV wherein m, n, p, q, r, X, $R^1$ to $R^{15}$ and Pro are as hereinbefore defined, and L is a suitable leaving group, such as tosylate, iodide, triflate, bromide, with a compound of formula $LiYR^{12}R^{13}$, wherein Y, $R^{12}$ and $R^{13}$ are as hereinbefore defined. The reaction is carried out in the presence of an organic solvent, such as THF, and with the addition of $BH_3$.

Compounds of formula (IV) may be prepared from the corresponding alcohol of formula (V)

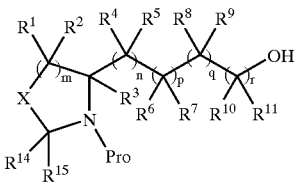

V wherein m, n, q, r, X, $R^1$ to $R^{15}$ and Pro are as herinbefore defined. The reaction is carried out with a suitable compound to give the desired leaving group, L. For example is the leaving group is tosyl, the reaction is carried out with for example tosyl chloride, in the presence of a base, for example triethylamine, and a suitable solvent, for example dichloromethane. A catalytic amount of 4-dimethylaminopyridine (DMdAP) may also be added.

Compounds of formula (V) are known in the literature (Ksander, G. M.; de Jesus, R.; Yuan, A.; Ghai, R. D.; Trapani, A.; McMarrin, C.; Bohacek, R., J. Med. Chem. 1997, 40, 495–505)

Compounds of formulae (II) and (IV) are also novel and accordingly form a further aspect of the invention.

A yet further aspect of the present invention provides a metal complex containing a ligand of formula (I), a metal and optionally other known ligands as may be required to stabilise the complex, e.g. chloride, acetate etc. Suitably, the metal is a transition metal; for example, the metal may be selected from the group consisting of Ni, Pd, Rh, Ir, Cu, Ag, Au and Zn.

A metal complex of the present invention may be of use in any chemical reaction requiring an asymmetric catalyst. Examples of such reactions include but are not limited to Heck type reactions, Suzuki type reactions, allylation reactions, cross-coupling reactions, hydrogenations, hydroformylations and isomerisation reactions. Therefore, a still further aspect of the invention provides a metal complex of the invention for use in asymmetric catalytic reactions. Alternatively, the invention provides the use of a metal complex of the invention in asymmetric catalytic reactions. Alternatively, there is provided a method for performing an asymmetric catalytic reaction, said method comprising the use of a metal complex of the invention.

The metal complex of the invention may be formed in situ from the ligand and a suitable precursor complex or salt of the metal. Therefore, a further aspect of the invention provides for the use of the ligand in combination with known metal complexes or salts in asymmetric catalysis.

The invention will now be described by way of example only.

(S)-N-tert-butoxycarbonyl-aspartic
acid diethyl ester (3)

Absolute ethanol (420 ml) was cooled in ice and acetyl chloride (71.4 ml, 1.03 mol) was added dropwise to generate HCl in situ. After the addition, the reaction was stirred for additional 30 minutes. L-Aspartic acid (33.27 g, 0.25 mol) was added in one portion and the solution heated slowly after dissolution to reflux. Refluxing was continued until the reaction was complete (TLC). The reaction mixture was then cooled to 25° C. and the solvent was removed under reduced pressure. Further drying under vacuum gave crude diethyl L-aspartate hydrochloride 2 as a viscous oil which crystallised on standing to a white solid, yield: 60 g (100%). This material was used without further purification. Spectral data for this sample were consistent with those given in the literature[1]. $^{13}$C NMR (75 MHz, d$_6$-DMSO) 169.1, 168.2, 70.0, 60.9, 48.5, 34.2, 14.9 and 13.9.

A sample of the diethyl L-aspartate hydrochloride 2 (575 g, 0.273 mol) was dissolved in water (59 ml) and dioxane (149 ml) then cooled to 0° C. Triethylamine (74 ml, 0.53 mol), then di-tert-butyl dicarbonate (74.99 g, 0.34 mol) were added with stirring. The reaction mixture was then heated at 50° C. overnight after which TLC (ethyl acetate-ethanol 1:1) indicated complete consumption of the starting material. The solvent was removed in vacuum, aqueous citric acid (150 ml, 10%, w/v) added to adjust the pH to 2–3. Diethyl ether (300 ml) was added and the organic phase was separated. The aqueous phase was extracted with ether (4×250 ml), the combined ether extracts washed with brine (100 ml), dried over Na$_2$SO$_4$, concentrated under vacuum to give 3 (78.8 g, 99%) as light yellow oil, which can be used without further purification. Spectral data for this sample were consistent with those given in the literature[2]. $^1$H NMR (300 MHz, CDCl$_3$) 5.48 (1H), 4.49 (m, 1H), 4.12 (m, 4H), 2.90 (dd,J=16.8 Hz,J=4.6 Hz), 2.76 (d,J=4.88 Hz, 1H), 1.46 (s, 9H), 1.21 (t,J=7.1 Hz, 3H), 1.20 (t,J=7.1 Hz, 3H); $^{13}$C NMR (75 MHz, CDCl$_3$) 170.9, 170.8, 155.4, 79.8, 61.6, 60.9, 49.9, 36.7, 28.2, 14.0 and 13.9.

(S)-2-(tert-butoxycarbonylamino)-1,4-butanediol (4)

A stirred solution of (S)-N-BOC diethyl Laspartate 3 (47.41 g, 0.16 mol) in absolute ethanol (770 ml) was cooled in ice, then sodium borohydride (60.8 g, 1.6 mol) was added in 10 g portions. The cooling bath was removed when the reaction subsided, and the reaction mixture was heated slowly to reflux for 1 h; after this time TLC (EtOAc-EtOH 3:1) analysis indicated complete consumption of the starting material. The reaction mixture was cooled to 25° C., and the lumps formed were broken-up to give a slurry that was poured into brine (450 ml). The mixture was filtered, the filtrate concentrated in vacuum to ca. 100 ml, and was extracted with ether (6×300 ml). The insoluble solid material was extracted by stirring in ether (4×1 L) for 2 h. The combined ether extracts were dried over MgSO$_4$, filtered and concentrated to give 4 as a colourless oil (24 g, 73%), which crystallised on standing. Spectral data for this sample were consistent with those given in the literature[2]. $^1$H NMR (200 MHz, d$_6$-DMSO) 6.45 (d, J=8.4 Hz, 1H), 4.57 (t,J=5.6 Hz, 1H), 4.35 (t,J=5.1 Hz, 1H), 3.40 (m, 4H), 3.23 (m, 1H), 1.62 (m, 1H), 1.40 (m, 1H), 1.36 (s, 9H); $^{13}$C NMR (50 MHz, d$_6$-DMSO) 155.5, 77.4, 63.5, 58.0, 49.6, 34.4, 2.83.

(S)-N-tert-butoxycarbonyl-4-(2-hydroxy)ethyl-2,2-dimethyloxazolidine (5)

2,2-Dimethoxypropane (87 ml, 0.707 mol) and p-toluenesulphonic acid monohydrate (1.33 g, 7 mmol) were added to a stirred solution of the diol 4 (14.39 g, 70 mmol) in dichloromethane (319 ml) at 25° C. The reaction was monitored by TLC (ethyl acetate-hexanes 2:1) until complete (36 h). The reaction mixture was then washed with aqueous NaHCO$_3$ (5%, 2×50 ml), brine (50 ml), dried (MgSO$_4$) and concentrated to form a colourless oil, which crystallised upon standing. The ratio of the desired five-membered ring product 5 to the undesired six-membered ring product 6 was 6.4:3.6. Recrystallisation from heptane gave 5 as colourless needles (8.2 g, 48%). Spectral data for this sample were consistent with those given in the literature[3]. $^1$H NMR (200 MHz, CDCl$_3$) 4.17 (m, 1H), 3.97 (m, 1H), 3.86–3.42 (m, 3H), 3.33 (br, 1H), 1.76 (m, 2H), 1.5 (s, 3H), 1.46 (s, 9H); $^{13}$C NMR (50 MHz, CDCl$_3$) 153.9, 93.6, 80.9, 68.2, 58.6, 53.9, 37.7, 27.7, 26.3, 243.

(S-N-tert-butoxycarbonyl-2,2-dimethyl-4-hydroxymethyl-1,3-oxazine (6)

A sample of pure 6 was isolated via flash chromatography using ethyl acetate/hexanes (3:1 v/v) as eluant. $^1$H NMR (200 MHz, CDCl$_3$) 3.37–3.77 (m, 5H), 1.62 (m, 2H), 1.35 (s, 9H), 1.24 (s, 3H), 1.22 (s, 3H); $^{13}$C NMR (50 MHz, CDCl$_3$) 155.0, 101.2, 79.1, 63.8, 57.9, 485, 35.7, 28.3, 24.7, 24.6.

(S)-2-(tert-butoxycarbonyl-4-(4-toluenesulfonyloxyethyl)-2,2-dimethyloxazolidine (7)

Dry, freshly crystallised p-toluenesulphonyl chloride (1.86 g, 9.8 mmol) and 4-dimethylaminopyridine (10 mg, 0.082 mmol) were added to a solution of alcohol 5 (2.00 g, 8.15 mmol) and triethylamine (2.6 ml, 18.75 mmol) in dichloromethane (20 ml) at 5° C. with stirring. The resulting solution was protected from moisture and kept at 5° C. until all the starting material 5 had reacted (33 h, TLC). A colourless solid, presumably triethylamine hydrochloride, crystallised out of the reaction, and was filtered away. The filtrate was diluted with dichloromethane to a volume of 90 ml, and washed with water (2×20 ml), brine (20 ml), dried over $Na_2SO_4$, and concentrated to give the crude tosylate 7 as white solid. This material was purified by dissolving in ether (ca. 330 ml), filtering through celite 545 on a wad of cotton wool to give 2.95 g (90%) of 7. $^1$H NMR (200 MHz, $CDCl_3$) 7.78 (m, 2H), 7.35 (d, 2H), 4.09 (m, 2H), 4.09 (m, 2H), 3.90 (m, 2H), 3.73 (m, 1H), 2.95 (m, 2H), 1.51 (s, 6H), 1.44 (s, 9H).

(S)-N-tert-butoxycarbonyl-4-ethylenediphenylphosphinoborane-2,2-dimethyloxazolidine (8)

n-Butyl lithium in hexanes (1.6 M, 17.1 ml, 27.4 mmol) was added to a solution of diphenylphosphine (4.52 g, 2.43 mmol) and THF (100 ml) at 0° C. The orange-red solution was stirred at 0° C. for 30 minutes. A solution of tosylate 7 (8.44 g, 21.1 mmol) in THF (60 ml) was then added dropwise to the solution of the diphenylphosphide anion at 0° C. The reaction mixture was stirred for another 30 minutes. Borane-THF complex (1 M, 26 ml, 26 mmol) was added to the solution at 0° C. and this was then stirred for an additional 20 minutes. The solvent was removed, and the remaining material was dissolved in ethyl acetate (600 ml) and washed with 1 M $HCl_{(aq)}$ (100 ml), sat. $NaHCO_3$ (100 ml), brine (100 ml), dried over $Na_2SO_4$, and filtered. The solvent was removed under reduced pressure. The residue was then purified by column chromatography on silica gel using ethyl acetate/hexane eluant (3:7 v/v) to give 8.1 g (18.9 mmol, 90%) of a colourless oil, which crystallised upon standing at 25° C. m.p. 95.0–9.65° C.; $R_f$ 0.81 (ethyl acetate/hexane, 1:1 v/v). $^1$H-NMR ($CDCl_3$, 300 MHz): 7.63 (m, 4H), 7.43 (m, 6H), 3.92 (m, 2H), 3.67 (m, 1H), 2.17 (m, 2H), 1.83 (m, 2H), 1.60 (s, 3H), 1.54 (s, 9H), 1.34 (s, 3H); $^{13}$C-NMR ($CDCl_3$, 75 MHz): 151.9, 131.9–132.1, 131.2, 128.9, 128.8, 94.0, 19.9, 67.0, 57.4, 28.3, 26.7, 22.9, 22.3, 21.8; $^{31}$P-NMR ($CDCl_3$, 121 MHz): 16.76 (br).

(S)-2-Phenyl-4-[(diphenylphosphino)ethyl]oxazoline (11a)

The protected phosphine 8 (500 mg, 1.17 mmol) was dissolved in 8 ml of methanol and cooled to 0° C. Gaseous HCl was bubbled through the reaction for 5–10 minutes. The methanol was removed under vacuum and the residue was dissolved in 8 ml of 1,2-dichloroethane. Triethylamine (1.5 ml, 9.3 mmol) and benzimidic acid ethyl ester hydrochloride[4] (230 mg, 1.24 mmol) were added, and the reaction was refluxed for 6 h. The solvent was removed giving colourless oil, and the crude product was purified by column chromatography on silica gel using ethyl acetate/hexane eluant (2:8 v/v) to afford oxazoline 11a (210 mg, 0.58 mmol, 50% yield) as a colourless solid. m.p. 52.5–54°; $R_f$ 0.76 (ethyl acetate/hexane, 3:7 v/v). $^1$H-NMR ($CDCl_3$, 300 MHz): 7.93 (d,J=7 Hz), 7.29–7.49 (m, 13H), 4.34–4.49 (m, 4H), 4.00 (dd,J=7.5 Hz,J=7.5 Hz), 2.24–2.34 (m, 2H), 2.07–2.15 (m, 2H), 1.67–1.85 (m, 4H); $^{13}$C-NMR ($CDCl_3$, 75 MHz): 163.7, 138.6, 138.3, 132.8, 132.6, 128.6, 128.5–128.2, 127.7, 72.2, 67.5 (d,J=13.5 Hz), 32.1(d,J=16.5 Hz), 24.1(d,J=11.5 Hz); $^{31}$P-NMR ($CDCl_3$, 121 MHz): −15.81 HRMS ($M^+$+1) m/z Calcd. for $C_{23}H_{23}NOP$: 360.15170. Found 360.15147.

General Procedure for Preparation of Oxazolines (11b–e)

(S)-2-Adamantyl-4-[(diphenylphosphino)ethyl] oxazoline (11b)

The protected phosphine 8 (500 mg, 1.17 mmol) was dissolved in 8 ml of methanol and cooled to 0° C. Gaseous HCl was bubbled through the reaction for 5–10 minutes, and the methanol was removed under vacuum. The residue was dissolved in 8 ml of 1,2-dichloroethane and triethylamine (0.44 ml, 4.1 mmol), catalytic 4-dimethylaminopyridine (2 mg), then adamantanecarbonyl chloride (256 mg, 1.28 mmol) were added and reaction was stirred for 12 h. Subsequently, borane-THF (1 M, 2 ml, 2 mmol) was added to the reaction mixture at 0° C., and this was stirred for 10 minutes. The reaction mixture was diluted with 15 ml of dichloromethane and washed with $HCl_{(aq)}$ (0.5 M, 10 ml×2) and brine (10 ml), dried over $Na_2SO_4$, filtered and concentrated. 1,4-Diazobicyclo[2.2.2]octane (656 mg, 5.85 mmol) and THF (8 ml) were added to this material. The reaction mixture was cooled to 0° C. and methanesulphonyl chloride (86 μl, 1.28 mmol) was added. The reaction was stirred at 25° C. for 4 h then heated to 50° C. for another 4 h. The resulting slurry was filtered and concentrated at reduced pressure, and the residue was flash chromatographed using ethyl acetate/hexane eluant (2:8 v/v) to give 370 mg (0.89 mmol, 75%) of the product 11b as an oil. $R_f$ 0.76 (ethyl acetate/hexane, 3:7 v/v)$^1$H-NMR ($CDCl_3$, 300 MHz): 7.43–7.48 (m, 4H), 7.34–7.41 (m, 6H), 4.14–4.23 (m, 2H), 3.81 (m, 1H), 2.18–2.24 (m, 1H), 2.03–2.08 (m, 3H), 1.90 (m, 3H), 1.64–1.83 (m, 12H); $^{13}$C-NMR ($CDCl_3$, 75 MHz): 173.5, 138.6, 138.2, 132.9, 132.7, 132.4, 128.6–128.3, 71.5, 66.4 (d, J=13.5 Hz), 39.6, 36.5, 35.1, 32.1(d,J=16.5 Hz), 28.1, 23.6 (d,J=11.5 Hz); $^{31}$P-NMR ($CDCl_3$, 121 MHz): −15.81. HRMS ($M^+$+1) m/z Calcd. for $C_{27}H_{33}NOP$: 418.22998. Found 418.22583.

(S)-2-tert-Butyl-4-[(diphenylphosphino)ethyl] oxazoline (11c)

This compound was prepared via the same method used for compound 11b, but beginning with 500 mg of 8, 117 mg (0.34 mmol, 30%) of the oxazoline 11c was produced as colourless oil. $R_f$ 0.68 (ethyl acetate/hexane, 3:7 v/v). $^1$H-NMR ($CDCl_3$, 300 MHz): 7.78 (s, 2H), 7.38–7.56 (m, 5H), 7.26–7.34 (m, 6H), 4.33–4.47 (m, 2H), 3.97 (t,J=7 Hz, 1H), 2.14–2.27 (m, 1H), 2.04–2.12 (m, 1H), 1.70–1.84 (m, 1H), 1.65–1.70 m, 1H), 1.33 (s, 18H); $^{13}$C-NMR ($CDCl_3$, 75 MHz): 174.0, 138.6, 138.2, 132.7, 132.4, 132.1, 128.6–128.3, 72.0, 66.6 (d,J=13.5 Hz), 33.2, 32.1(d,J=16.5 Hz), 27.8, 23.6 (d,J=11.5 Hz); $^{31}$P-NMR ($CDCl_3$, 121 MHz): −15.37. HRMS ($M^+$+1) m/z Calcd. for $C_{21}H_{27}NOP$ 340.18303. Found 340.18281.

(S)-2-(3,5-Di-tert-butylphenyl)-4-[(diphenylphosphino)ethyl]oxazoline (11d)

This compound was prepared via the same method used to prepare 11b. Beginning with 500 mg of 8, 227 mg (0.48 mmol, 41%) of the oxazoline 11d was produced as colourless oil. $R_f$ 0.77 (ethyl acetate/hexane, 3:7 v/v). $^1$H-NMR ($CDCl_3$, 300 MHz): 7.38–7.44 (m, 4H), 7.27–7.37 (m, 6H), 4.21 (m, 1H), 4.12 (m, 1H), 3.80 (dd,J=63 Hz, J=7.8 Hz), 2.14 (m, 1H), 2.01 (m, 1H), 1.60 (m, 2H), 1.57 (s, 9H); $^{13}$C-NMR ($CDCl_3$, 75 MHz): 164.4, 150.9, 138.5, 138.3, 132.9, 132.8, 132.6, 128.7–128.4, 127.0, 125.6, 122.5, 72.0, 67.5 (d,J=13.5 Hz), 34.9, 32.1(d,J=16.5 Hz), 31.4, 24.0 (d,J=12.0 Hz); $^{31}$P-NMR ($CDCl_3$, 121 MHz): −15.20.

HRMS (M⁺+1) m/z Calcd. for $C_{31}H_{39}NOP$ 472.27693. Found 472.27524.

(S)-2-Triphenylmethyl-4-[(diphenylphosphino)ethyl]oxazoline (11e)

This compound was prepared via the same method for compound 11b. Beginning with 500 mg of 8, 191 mg (0.36 mmol, 31%) of the oxazoline 11e was produced as colourless oil. $R_f$ 0.71 (ethyl acetate/hexane, 3:7 v/v). ¹H-NMR (CDCl₃, 300 MHz): 7.25–7.50 (m, 25H), 4.35 (m, 2H0, 4.02 (m, 1H), 2.21 (m, 1H), 2.10 (m, 1H), 1.77 (m, 2H); ¹³C-NMR (CDCl₃, 75 MHz): 169.6, 143.4, 138.4, 138.2, 132.9, 132.6, 1324, 130.1–126.5, 71.9, 66.8(d,J=13.5 Hz), 61.4, 31.8 (d,J=16.5 Hz), 23.7 (d,J=11.5 Hz); ³¹P-NMR (CDCl₃, 121 MHz): −15.51.

REFERENCES 1. (a) Williams, R. M.; Im, M-N., J. Am. Chem. Soc. 1991, 113, 9276–9286. (b) Williams, R. M.; Sinclair, P. J.; Zhai, D.; Chen, D., J. Am. Chem. Soc. 1988, 110, 1547–1557.
2. Deaimoni, G.; Dusi, G.; Quadrelli, P.; Righetti, P., Tetrahedron, 1995, 51, 4131–4144.
3. Ksander, G. M.; de Jesus, R.; Yuan, A.; Ghai, R. D.; Trapani, A.; McMartin, C.; Bohacek, R., J. Med. Chem. 1997, 40, 495–505.
4. Meyers, A. I.; Schmidt, W; McKennon, M. J., Synthesis, 1993, 250–262.

I claim:

1. A compound of formula (I)

wherein
  m is 1, 2, 3 or 4;
  n, p, q, r are independently zero or 1 provided that at least one of n, p, q and r is 1;
  X is O, S, Se, $CH_2$, NH;
  Y is N, P, As, S;
  R is H; a straight, branched or cyclo alkyl optionally substituted by one or more groups independently selected from alkyl, aryl, halo, alkoxy, amine, phosphine, ether; aryl optionally substituted by one or more groups independently selected from alkyl, aryl, halo, alkoxy, amine, phosphine, ether; ferrocenyl; a thioalkyl group; a thioaryl group; or R is part of a polymeric structure, for example polyacrylic acid;
  $R^1$ to $R^{13}$ are independently selected from H; a straight, branched or cyclo alkyl optionally substituted by one or more groups independently selected from alkyl, aryl, halo, alkoxy, amine, phosphine, ether; aryl optionally substituted by one or more groups independently selected from alkyl, aryl, halo, alkoxy, amine, phosphine, ether.

2. A compound according to claim 1, wherein m is 1 or 2.
3. A compound according to claim 1, wherein at least two of n, p, q and r are 1, the remaining two being zero or 1.
4. A compound according to claim 1, wherein X is O, S, $CH_2$ or NH.
5. A compound according to claim 1 wherein Y is P, N or S.
6. A compound according to claim 1 which is a compound of formula (IA)

wherein m, X, Y, R, and $R^1$ to $R^5$ and $R^{12}$ and $R^{13}$ are as hereinbefore defined.

7. A compound according to claim 1 which is a compound of formula (IB)

wherein m, X, Y, R and $R^1$ to $R^7$ and $R^{12}$ and $R^{13}$ are as hereinbefore defined.

8. A compound according to claim 1 which is a compound of formula (IC)

wherein m, X, Y, R and $R_1$ to $R^9$ and $R^{12}$ and $R^{13}$ are as hereinbefore defined.

9. A compound according to claim 1 which is a compound of formula (ID)

wherein m, X, Y, R and $R^1$ to $R^{13}$ are as hereinbefore defined.

10. compound according to claim 1 which is a compound of structure

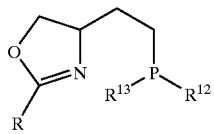

wherein R is $C_{1-4}$ alkyl optionally substituted by one or more groups selected from phenyl or halo; phenyl optionally substituted by one to five substituents selected from the group consisting of halo, $C_{1-4}$ alkyl, $C_{1-4}$ alkoxy or nitro; ferrocenyl or adamantyl; and $R^{12}$ and $R^{13}$ are Ph or cyclohexyl.

11. A compound according to claim 1 which is a compound selected from the group consisting of:

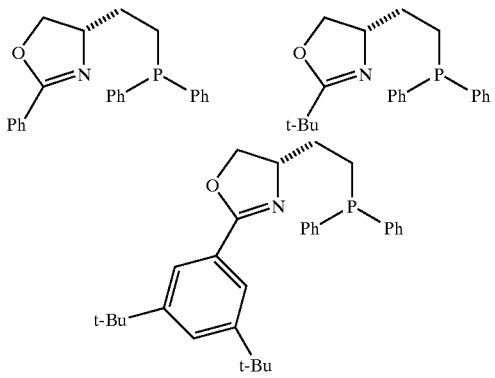

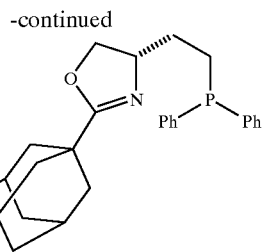

12. A process for the preparation of a compound according to claim 1, said process comprising the reaction of a compound of formula (II)

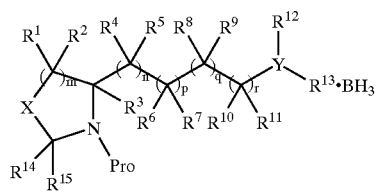

II wherein m, n, p, q, r, X, Y and $R^1$ to $R^{13}$ are as hereinbefore defined; $R^{14}$ and $R^{15}$ are alkyl groups which may be the same of different and Pro is a nitrogen protecting group, with a compound of formula (III)

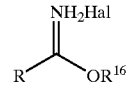

III wherein R is as hereinbefore defined, $R^{16}$ is an alkyl group, and Hal is a halogen atom.

* * * * *